United States Patent [19]

Spangler

[11] Patent Number: 5,382,224

[45] Date of Patent: Jan. 17, 1995

[54] DROP FOOT BRACE

[76] Inventor: Harry V. Spangler, 510 W. Harmont, Phoenix, Ariz. 85021

[21] Appl. No.: 959,627

[22] Filed: Oct. 13, 1992

[51] Int. Cl.⁶ .............................................. A61F 5/00
[52] U.S. Cl. ........................................ 602/23; 602/28
[58] Field of Search ................. 602/28, 23, 24, 27, 602/61, 62; 128/869, 882

[56] References Cited

U.S. PATENT DOCUMENTS

| 2,439,100 | 4/1948 | Richards | 602/28 |
| 2,525,237 | 10/1950 | Park | 602/28 |
| 2,536,454 | 1/1951 | McIntyre | 602/28 |
| 2,874,690 | 2/1959 | Cowgill | 602/28 |
| 3,859,991 | 1/1975 | Theodores | 602/28 |
| 4,329,982 | 5/1982 | Heaney | 602/28 |
| 5,112,296 | 5/1992 | Beard | 602/28 |

Primary Examiner—Michael A. Brown

[57] ABSTRACT

A brace for individuals with a medical condition known as a drop foot. The brace holds the foot in a level or horizonal position. The brace is attached to the ankle and shoe. A leather strap is attached to the ankle. The link between the leather strap and shoe has a swivel, spring and other connecting parts which provides the link to turn freely and provides the foot up and down motion. The brace can be attached and removed in seconds to and from the ankle and shoe. The brace can be colored to match the color of the apparel an individual is wearing.

1 Claim, 5 Drawing Sheets

DROP FOOT BRACE

BACKGROUND OF THE INVENTION

There are several diseases and injuries to nerves which causes what is medically known as a "drop foot". With this condition the foot hangs down and can not be raised. It is difficult to walk with this condition. The toe of the shoe, when walking with this condition, often hits the slightest rise in a walk way and other places causing the individual to stumble and sometimes fall. To correct this condition a leg device known as a "drop foot brace" is attached to the shoe to hold the foot in a horizontal or 90 degree position. In previous designed braces some have unsightly metal elements running up each side of the leg to or above the calf of the leg. Others braces have unsightly straps running from just below the knee to the shoe. Because the braces are, in effect, custom made, they are also quite expensive. Furthermore, in most cases, the brace becomes part of the shoe, so that the only pair of shoes which the individual can use is a pair which forms part of the brace. It becomes quite expensive to own more than one brace for different types of shoes. In addition, the braces have either metal or straps running from the shoe up to a strap or fastnet which fits just below the knee and at or above the calf of the leg. These braces have a downward pull on the calf of the leg or have a mechanical stress which causes stress or irritation to the calf of the leg. Some braces feel as though you had your leg in a cast. These and other difficulties experience with the prior art devices have been eliminated in a novel and new manner by an ankle attached and forward pulling brace as stated in the present invention.

It is, therefore, the primary object of the invention to provide a drop foot brace which is small, inexpensive compact with a natural feel when walking and can be quickly changed to many shoes of various types and colors, pleaseing in appearance and yet which performs its function satisfactorily.

Another object of the present invention is the provision of a drop foot bace, in two parts, which can be used with dress shoes; working shoes; walking shoes; garden shoes; sports shoes; and most other shoes and the brace can be changed to another shoe in 15 seconds or less without any special skills.

Another object of the present invention was to design a drop foot brace in two parts with the provision that the shoe attachment portion was seperate from the primary brace and could be quickly attached to several shoes and, if desired, could be quickly removed from the shoe without any apparent damage to the shoe.

A further object of the present invention was to design a comfortable drop foot brace in two parts. One part is ankle attached, rather than attached at or above the calf, with a forward pulls rather than a downward pull, to take the stress or irritation off the calf of the leg and the other part of the brace is seperately attached to the shoe or shoes for a quick change from one shoe to another shoe.

Another object of the present invention is, in addition to maintaining the foot in a horizontal or 90 degree position, to allow the foot up and down motion for natural walking and for walking up and down hills and allowing the foot to move in lateral directions when getting in and out of cars and other confined spaces.

Another object of the present invention is to provide a drop foot brace with a number of simple and inexpensive parts that are interchangeable and can be readily replaced at little cost by the individual with the drop foot.

A still further object of the present invention is to design a drop foot brace which is simple in construction which can be inexpensively manufactured from common available material with little or no maintenance. Another object of the present invention is to have a comfortable small compact brace which would be pleasing in appearance to men, women and children which can be colored blue, browns black, white or any other color to match the color of the shoe, socks or pants and is acceptable in appearance even when wearing walking shorts. Still another object of the present invention is to have the brace compact in order to place one or two additional braces in a suitcase while traveling.

SUMMARY OF THE INVENTION

In general, the present invention consist of an ankle attached leg brace having a leather strap adapted to be attached to the ankle of the individual with a drop foot. The leather strap attached to the ankle is connected to the shoe through a linkage consisting of a cotter pin, washer, plug, tube, swivel, spring, eye screw, wood connector and safety hook. This part of the brace is seperate and apart from the shoe attachment portion of the brace. The shoe attachment portion of the brace consist of a nylon cord, stud metal fasteners and metal fasteners inserted into the sole of a shoe. The metal fastners are inserted into the stud metal fasteners which attaches the nylon cord to the shoe. The safety hook, on the linkage from the leather strap, is attached to the nylon cord on the shoe when brace is being used.

DESCRIPTION OF THE PREFERRED EMBODIMENT

Figure 1:
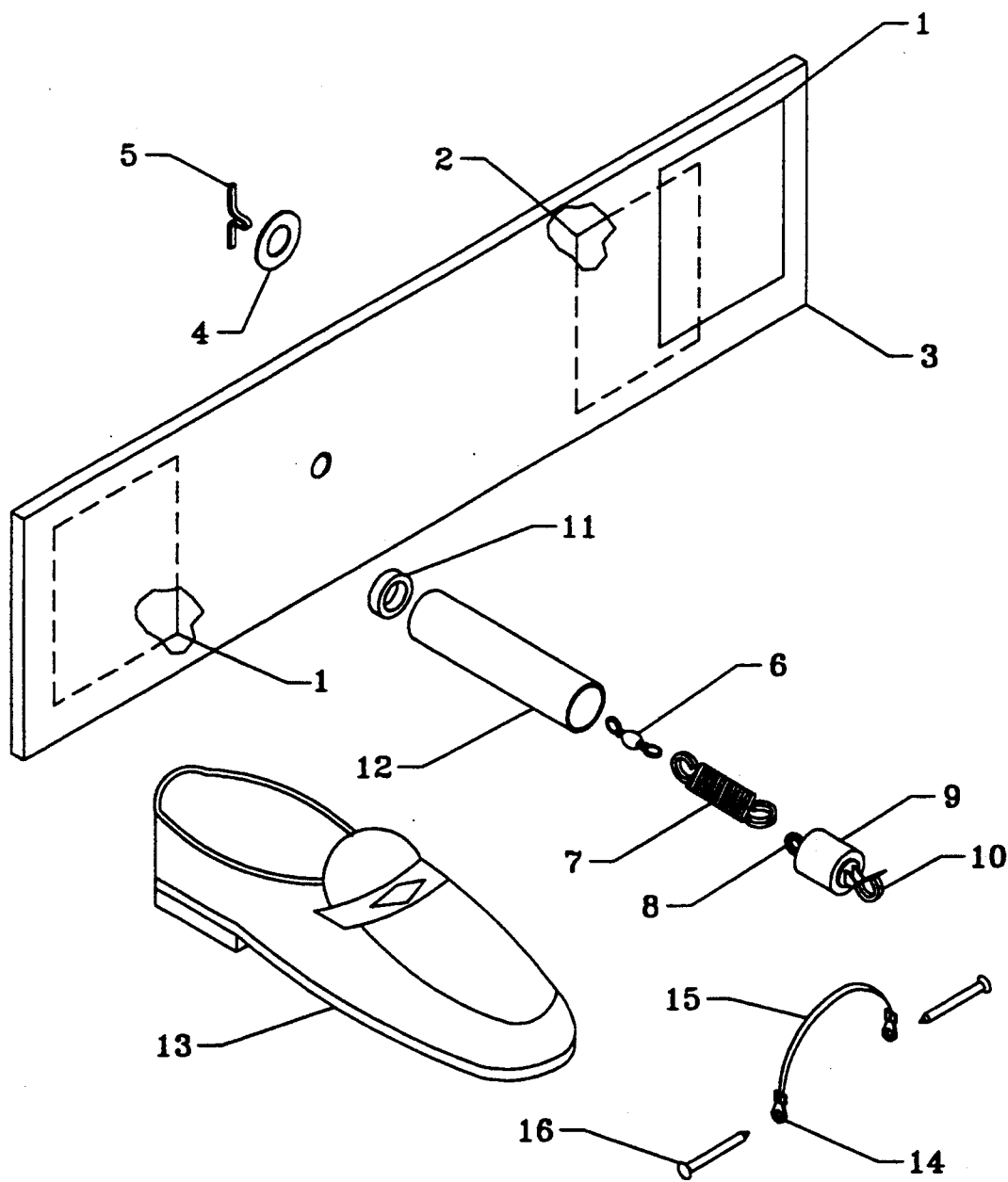
FIG. 1 is an exploded assembly of the present invention.
Figure 2:
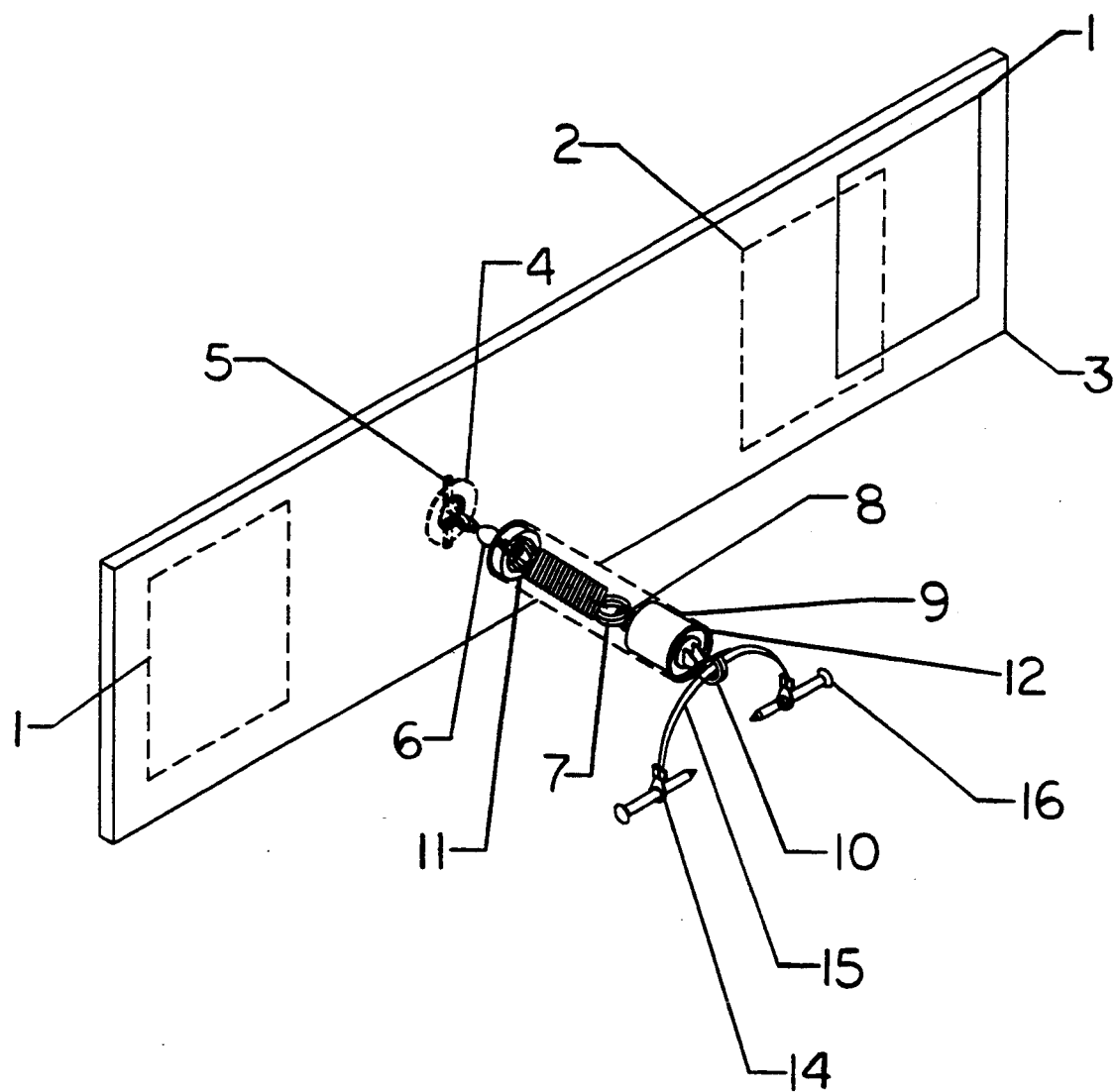
FIG. 2 is an assembly view of leather strap and linkage to shoe attachment.
Figure 3:
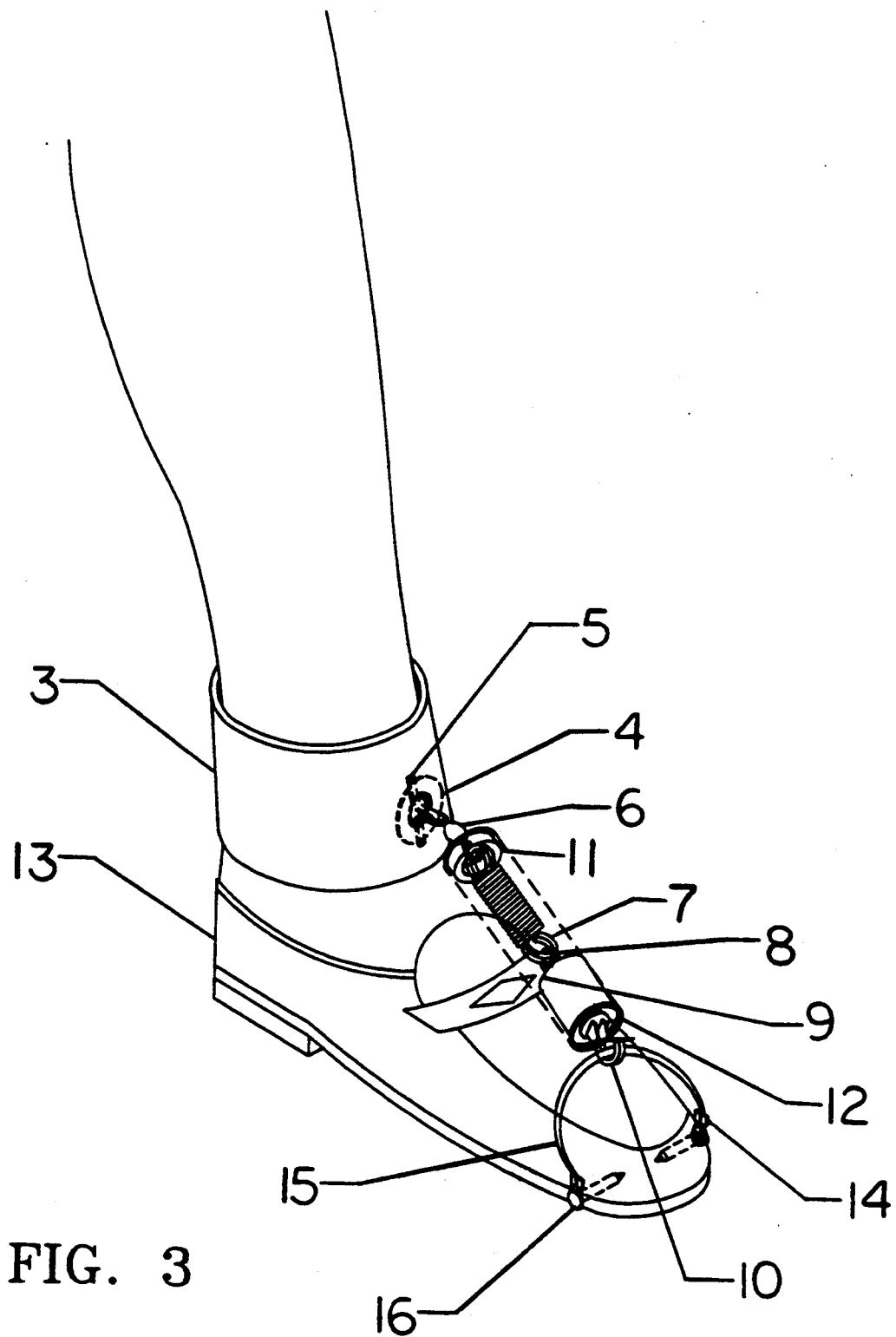
FIG. 3 is an assembly view showing the present invention in working position.

Referring to FIG. 1, wherein are shown the general features and parts of the invention and shown assembled in FIG. 2. FIG. 1 shows leather strap 3, with Hook and Loop Fastener (Velcro) 1, on opposite ends and opposite sides of leather strap 1, which are machine sewn to leather strap 1. Sponge 2, is glued to inside of strap 3. FIGS. 1-5 shows hole in leather strap 3. Referring to FIG. 1, safety hook 10, is screwed into connector 9, eye hook 8, is screwed into connector 9, spring 7, is attached to eye hook 8, spring 7, is attached to swivel 6. Plug 11, is glued to inside of tube 12. The assembled swivel 6, spring 7, eye hook 8, connector 9, and safety hook 10, are inserted into the opening of tube 12. Swivel 6, will protrude through the opening in plug 11. Referring now to FIG. 2 and 3, swivel 6, is inserted through hole in leather strap 3, swivel 6, is inserted through hole in washer 4, cotter pin 5, is inserted through hole in swivel 6. The leg portion of the brace now completly assembled as shown in FIG. 2.

Figure 4:
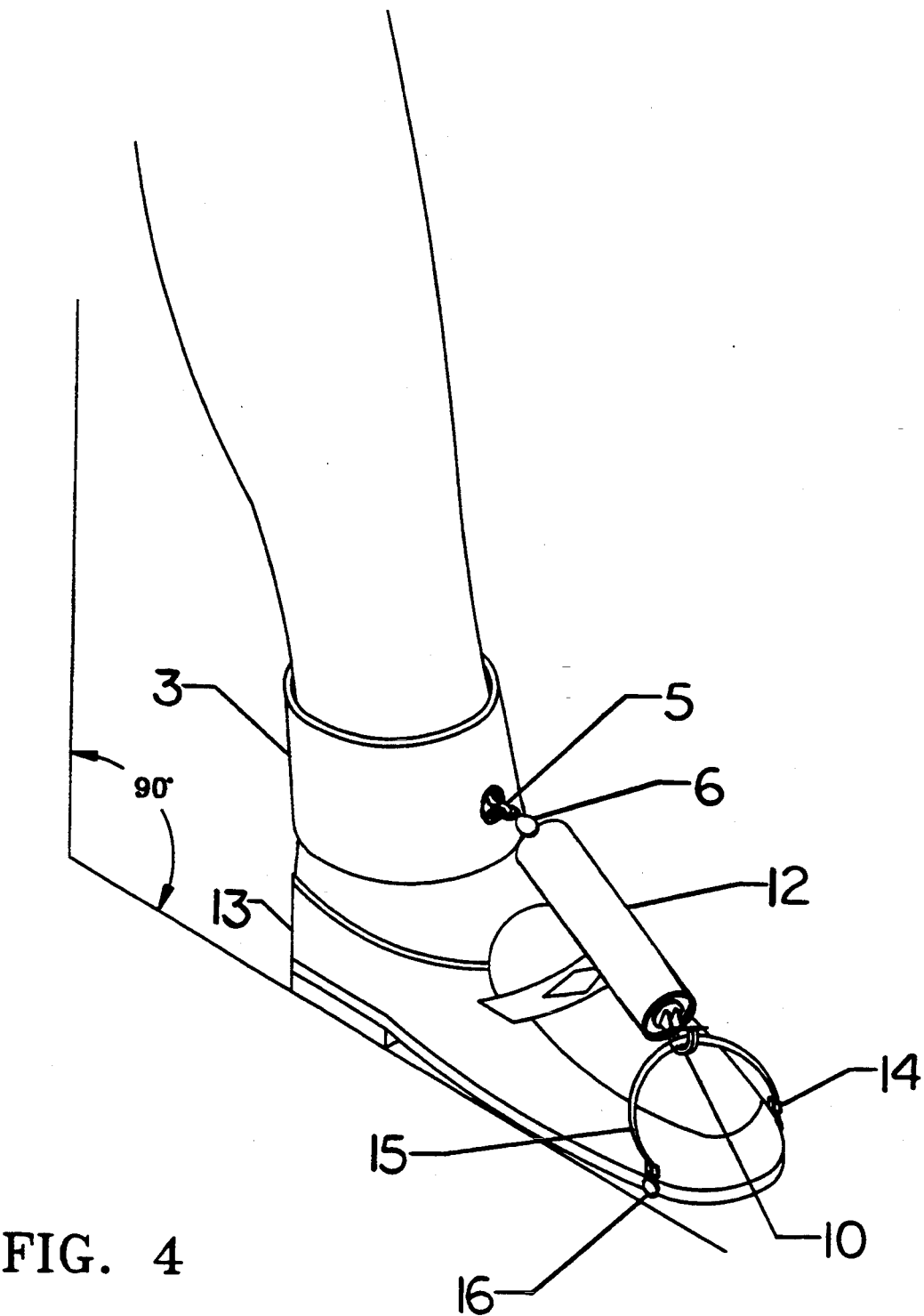
FIG. 4 is a view with leg and shoe in a standing position with the leg and shoe at 90 degrees to each other.
Figure 5:
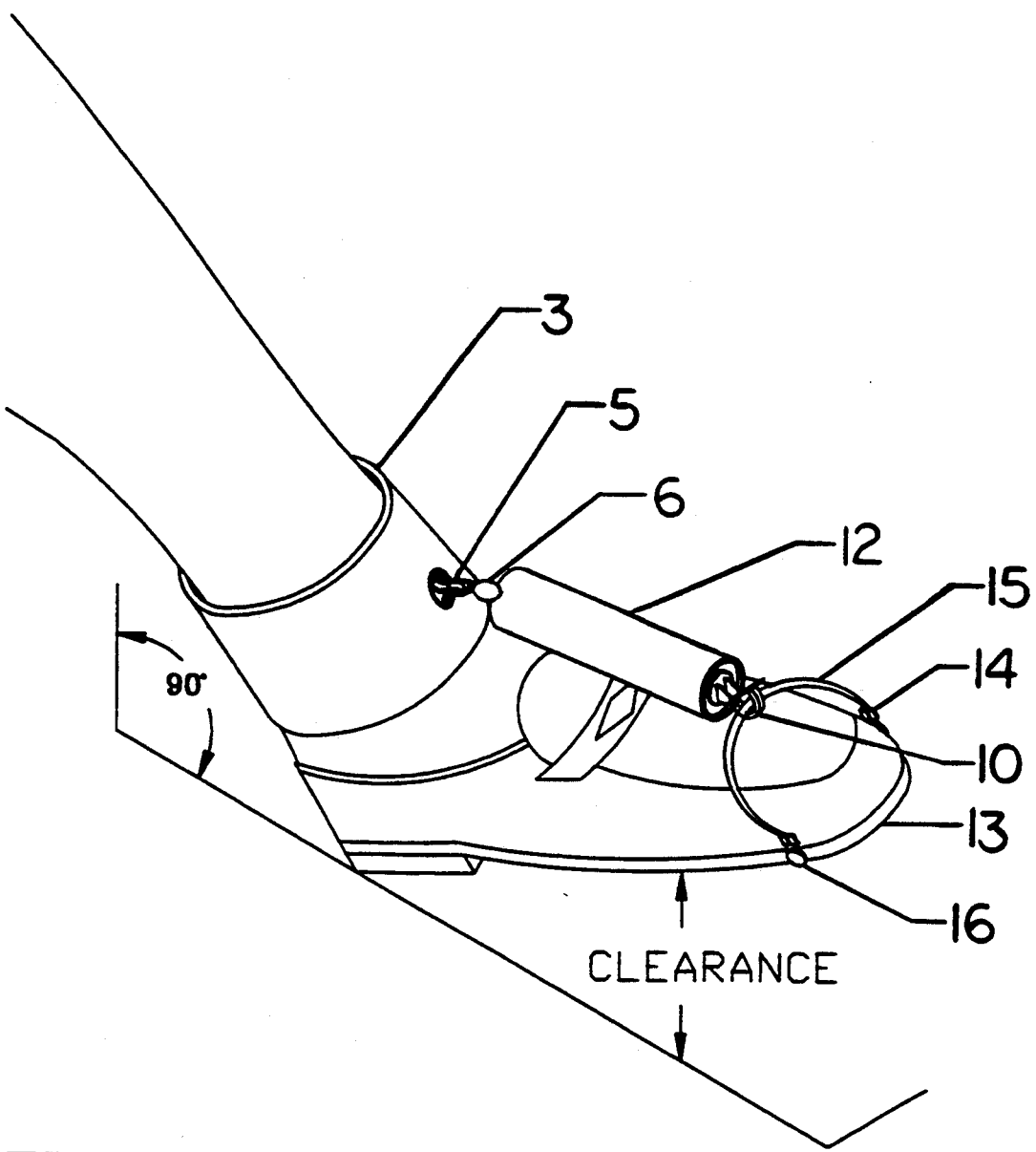
FIG. 5 is a view of the leg and shoe in a walking position with the toe raised to maintain a 90 degree angle when the leg is swung forward.

Referring to FIG. 1, for the shoe assembly portion of the brace, nylon cord 15, is attached to metal stud fasteners 14. FIG. 2, shows metal fasteners 16, inserted through holes in metal stud fasteners 14. FIG. 3, 4 and 5, shows metal fastners 16, inserted into sole of shoe 13. The shoe assembly portion of the brace is now complete.

The operation of the invention will now be readily understood in view of the above description. The safety hook 10, is snapped over nylon cord 15, as shown in FIG. 3, 4 and 5. Leather strap 3, is placed around ankle and fastened with Hook and Loop Fastener (Velcro) 1, as shown in FIG. 3, 4 and 5. The individual with a drop foot is now ready to walk with the brace affixed to ankle and shoe. FIG. 4, shows individual standing with leg and foot at right angle or 90 degrees. FIG. 5, shows individual walking with leg swung forward and brace holding foot at 90 degres with clearance between toe and a level walking surface.

While there has been described what is presently believed to be the preferred embodiment of the invention, those skilled in the art will realize that changes and modifications may be made thereto without departing from the spirit of the invention, and it is intended to claim all such changes and modifications as fall within the true scope of the invention.

The invention having been thus described, what is claimed as new and desired to secure by Letters Patent is:

1. A leg brace comprising a leather strap adapted to be placed around a patient's ankle;
   a linkage means connected to said leather stap by a swivel means, said linkage means including a spring attached to said swivel means;
   a connector attached to said spring;
   a tube that encases said swivel means, said spring, and said connector;
   a flexible, nylon cord attachable to a shoe, said nylon cord is adapted to be connected to said shoe by a fastening means, said nylon cord is attached to said linkage means by a fastening means.

* * * * *